United States Patent
Hill et al.

(10) Patent No.: US 6,920,875 B1
(45) Date of Patent: Jul. 26, 2005

(54) AVERAGE VOLUME VENTILATION

(75) Inventors: Peter D. Hill, Monroeville, PA (US); Michael H. Kissel, Harrison City, PA (US); John Frank, Harrison City, PA (US)

(73) Assignee: Respironics, Inc., Murrysville, PA (US)

( * ) Notice: Subject to any disclaimer, the term of this patent is extended or adjusted under 35 U.S.C. 154(b) by 0 days.

(21) Appl. No.: 09/586,054

(22) Filed: Jun. 2, 2000

Related U.S. Application Data

(60) Provisional application No. 60/139,424, filed on Jun. 15, 1999.

(51) Int. Cl.[7] .............................................. A62M 16/00
(52) U.S. Cl. ............................ 128/204.18; 128/204.21; 128/204.22; 128/204.23; 128/204.26
(58) Field of Search ....................... 128/204.26, 204.18, 128/204.21, 204.23, 204.22

(56) References Cited

U.S. PATENT DOCUMENTS

| | | | |
|---|---|---|---|
| 5,551,419 A | * | 9/1996 | Froehlich et al. ...... 128/204.23 |
| 5,632,269 A | * | 5/1997 | Zdrojkowski .......... 128/204.21 |
| 5,794,615 A | | 8/1998 | Estes |
| 5,803,065 A | | 9/1998 | Zdrojkowski et al. |
| 5,865,173 A | * | 2/1999 | Froehlich ............... 128/204.21 |
| 5,931,162 A | * | 8/1999 | Christian ............... 128/204.23 |
| 6,041,780 A | * | 3/2000 | Richard et al. ........ 128/204.18 |
| 6,099,481 A | * | 8/2000 | Daniels et al. ............. 600/538 |
| 6,253,765 B1 | * | 7/2001 | Hognelid et al. ...... 128/204.18 |
| 6,532,957 B2 | * | 3/2003 | Berthon-Jones ........ 128/204.21 |

OTHER PUBLICATIONS

Nellcor Puritan Bennett, "BreathStar 340 Ventilator Manual", Nov., 1998, Revision A, Initial Release.

* cited by examiner

*Primary Examiner*—Glenn K. Dawson
*Assistant Examiner*—Darwin P. Erezo
(74) *Attorney, Agent, or Firm*—Michael W. Haas

(57) ABSTRACT

A ventilator supplies a plurality of volumes of fluid to a patient during a like plurality of inhalations by the patient. Each volume of fluid is supplied at an inspiratory positive airway pressure during a corresponding inhalation by the patient. A volume of fluid received by the patient is determined for each of the plurality of inhalations by the patient and an average volume of fluid received by the patient during each of the plurality of inhalations is determined. The average volume of fluid received by the patient during each inhalation is compared to a predetermined target volume and the inspiratory positive airway pressure each volume of fluid is supplied to the patient is adjusted as a function of the comparison.

5 Claims, 3 Drawing Sheets

AVERAGE VOLUME VENTILATION

CROSS-REFERENCE TO RELATED APPLICAIONS

This application claims priority under 35 U.S.C. § 119(e) from U.S. provisional patent application No. 60/139,424 filed Jun. 15, 1999.

BACKGROUND OF THE INVENTION

1. Field of the Invention

The present invention pertains to a ventilator and a method of controlling a ventilator to supply a desired inspiratory target volume of fluid, such as air or an oxygen mixture, to a patient.

2. Description of the Related Art

It is known to utilize a conventional ventilator to deliver a fluid, such as air or an oxygen mixture, to a patient in a volume targeted ventilation mode in which the ventilator attempts to deliver to the patient, during inspiration, a preset volume of fluid. To adjust the volume of fluid delivered to the patient during inspiration to achieve this target volume during each inspiration, the ventilator adjusts the pressure of the fluid supplied to the patient. For example, for a given inspiratory phase in a plurality of respiratory cycles, increasing or decreasing the pressure increases or decreases the volume of fluid delivered to the patient, respectively.

Volume ventilators that operate in a volume targeted ventilation ("VTV") mode monitor the actual volume of fluid delivered to the patient during an inhalation and increase or decrease, as needed, the pressure at which the fluid is delivered to the patient to meet a target volume of fluid. A problem with adjusting the volume of fluid delivered for one inhalation based upon a difference between the volume of fluid delivered during a previous inhalation and the target volume of fluid is that large differences between the previous volume and the target volume can result in large changes in the volume of fluid delivered to the patient. Such changes can result in the patient experiencing uncomfortable and unnatural variations in the volume of fluid received from one inhalation to another.

It is also known to operate a ventilator in a volume assured pressure support ("VAPS") mode in which the pressure is controlled by the ventilator in a manner so as to ensure that a set minimum volume is always delivered to the patient during each breath. In this mode of volume ventilation, if, during an inspiratory phase, the patient's inspiratory flow is not sufficient to provide the set volume for that breath, the ventilator transitions to a volume controlled mode of operation and increases the pressure of the fluid flow to the patient to meet this set volume. This typically occurs at the middle or near the end of the inspiratory phase when the ventilator determines that the patient's inspiratory rate will not be sufficient to achieve the set volume for that breath. Because this increase in pressure typically occurs near the end of the breath, when the patient is most likely to want to exhale, this mode of ventilation can be uncomfortable to the spontaneously breathing patient.

SUMMARY OF THE INVENTION

Accordingly, it is an object of the present invention to provide a ventilator and method of controlling a ventilator that overcomes the shortcomings of conventional ventilators and conventional modes of ventilation. This object is achieved according one embodiment of the present invention by providing a method for adjusting a volume of fluid supplied to a patient from one inhalation to the next in a manner that is comfortable for the patient and responsive to the patient's changing respiratory demands. This method includes supplying a plurality of volumes of fluid to a patient during a like plurality of inspiratory phases of the patient. Each volume of fluid is supplied at an inspiratory positive airway pressure ("IPAP") during a corresponding inspiratory phase, which is either triggered by the patient or by the ventilator. For each inspiratory phase, a volume of fluid received by the patient is determined. An average volume of fluid received by the patient is determined by taking an average of the volumes of fluid received by the patient during the plurality of inspiratory phases. The average volume of fluid received by the patient is compared to a predetermined target volume and the inspiratory positive airway pressure is adjusted based on this comparison.

In a further embodiment of the present invention determining the volume of fluid received by the patient for each inspiratory phase includes determining an estimated leak volume of fluid for each inspiratory phase. For each inspiratory phase, the estimated leak volume of fluid is subtracted from the supplied volume of fluid to obtain the volume of fluid received by the patient.

In an exemplary embodiment of the present invention, adjusting the inspiratory positive airway pressure based on the comparison between the average volume of fluid received by the patient and a predetermined target volume includes increasing the inspiratory positive airway pressure or decreasing the inspiratory positive airway pressure when the average volume is less than or greater than the predetermined target volume, respectively. Adjusting the inspiratory positive airway pressure based on this comparison can also include maintaining the inspiratory positive airway pressure when the average volume is within an offset volume of the predetermined target volume.

It is a further object of the present invention to provide a method of supplying a desired volume of fluid to a patient. This method includes supplying a first volume of fluid to the patient at a first inspiratory positive airway pressure. A first volume of fluid received by the patient is determined for the first volume of fluid supplied to the patient. A second volume of fluid is supplied to the patient at the first inspiratory positive airway pressure. A second volume of fluid received by the patient is determined for the second volume of fluid supplied to the patient. A first average volume of fluid received by the patient is determined from the first and second volumes of fluid received by the patient. The first average volume of fluid is compared to a predetermined target volume and the first inspiratory positive airway pressure is adjusted to a second inspiratory positive airway pressure as a function of the comparison.

This above-described method can also include supplying a third volume of fluid to the patient at the second inspiratory positive airway pressure and determining a third volume of fluid received by the patient for the third volume of fluid supplied to the patient. A second average volume of fluid received by the patient is determined as a function of the second and third volumes of fluid received by the patient. The second average volume is compared to the predetermined target volume and the second inspiratory positive airway pressure is adjusted to a third inspiratory positive airway pressure as a function of the comparison.

At least two of the first, second, and third inspiratory positive airway pressures can be the same. The second inspiratory positive airway pressure is greater than the first inspiratory positive airway pressure when the first average volume is less than the predetermined target volume. The second inspiratory positive airway pressure is less than the first inspiratory positive airway pressure when the first average volume is greater than the predetermined target volume. The second inspiratory positive airway pressure is the same as the first inspiratory positive airway pressure when the first average volume is within a predetermined offset volume of the predetermined target volume. At least one of the first volume of fluid and the second volume of fluid received by the patient can be determined using regression analysis.

The above object of providing a ventilator that overcomes the shortcomings of conventional ventilators is accomplished according to one embodiment of the present invention by providing an apparatus for supplying fluid to a patient that includes a pressure generating system that provides a flow of fluid at a variable pressure or a variable flow. A patient circuit operatively coupled to the pressure generating system delivers the flow of fluid to a patient. An interface device coupled to the patient circuit communicates the flow of fluid to the airway of the patient. At least one sensor in the apparatus detects a parameter indicative of a volume of fluid delivered to the patient. In addition, a controller receives signals from the sensor and controls the pressure generating system. In particular, the controller (a) determines, for each inspiratory phase of a respiratory cycle of the patient, a volume of fluid received by the patient based on the parameter indicative of a volume of fluid delivered to the patient provided by the sensor, (b) determines an average volume of fluid received by the patient over a plurality of inspiratory phases, (c) compares the average volume of fluid received by the patient to a predetermined target volume, and (d) causes the pressure generating system to adjust the pressure or the rate of flow of fluid output thereby based on this comparison.

The above object of providing a ventilator that overcomes the shortcomings of conventional ventilators is accomplished according to another embodiment of present invention by providing an apparatus for supplying fluid to a patient that includes a system for supplying a plurality of volumes of fluid to a patient during a like plurality of inspiratory phases of the patient's respiratory cycles, with each volume of fluid supplied at an inspiratory positive airway pressure during a corresponding inspiratory phase. The system also determines, for each inspiratory phase, a volume of fluid received by the patient. The system further determines an average volume of fluid received by the patient from the volumes of fluid received by the patient during the plurality of inspiratory phases. Finally, the system compares the average volume to a predetermined target volume, and adjusts the inspiratory positive airway pressure based on this comparison.

The above object of providing a ventilator that overcomes the shortcomings of conventional ventilators is accomplished according to yet another embodiment of present invention by providing an apparatus for supplying fluid to a patient that includes a system for supplying a first volume of fluid to a patient at a first inspiratory positive airway pressure, and a system for determining, for the first volume of fluid supplied to the patient, a first volume of fluid received by the patient. The supply system supplies a second volume of fluid to the patient at the first inspiratory positive airway pressure, and the determining system determines, for the second volume of fluid supplied to the patient, a second volume of fluid received by the patient. An averaging system determines, based on the first and the second volumes of fluid received by the patient, a first average volume of fluid received by the patient. A comparing system compares the first average volume to a predetermined target volume, and an adjusting system adjusts the first inspiratory positive airway pressure to a second inspiratory positive airway pressure based on the comparison of the first average volume to the predetermined target volume.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE PRESENTLY PREFERRED EMBODIMENTS OF THE INVENTION

Figure 1:
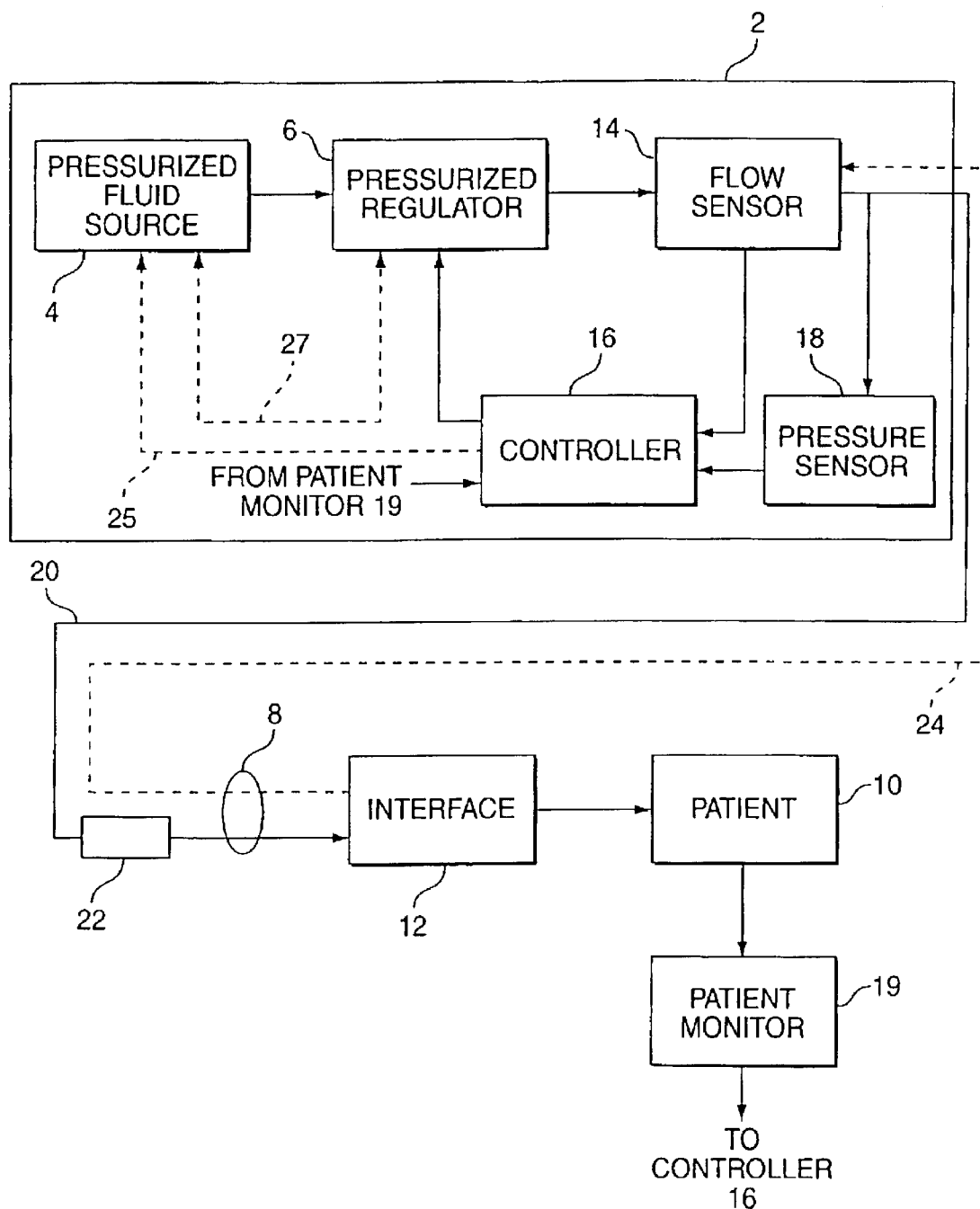
FIG. 1 is a schematic diagram of a ventilator connected to a patient via a circuit and an interface.

FIG. 1 illustrates an exemplary embodiment of a pressure support system or ventilator 2 according to the principles of the present invention. As used herein, the term "ventilator" refers to any device that delivers a flow of breathing gas to a patient at a variable pressure, and is not intended to be limited to a life support ventilating system. An example of a pressure support system that provides a variable pressure to the patient based on patient's respiratory cycle that is not necessarily used for life support purposes is the pressure support system taught in U.S. Pat. Nos. 5,148,802 and 5,433,193, both to Sanders et al., the contents of which are incorporated by reference into the present application.

Ventilator 2 includes a source of pressurized fluid 4 and a pressure regulator 6 connected to receive pressurized fluid from source of pressurized fluid 4. Pressure regulator 6 regulates the pressure of the pressurized fluid supplied to a patient circuit 8, which conveys the pressure regulated fluid to a patient 10 via a patient interface device 12. A sensor 14 detects a parameter associated with the fluid flow in patient circuit 8 or in interface device 12 that can be used to determine a volume of fluid supplied to the patient from pressure regulator 6 and provides to a controller 16 a signal indicative this parameter.

In an exemplary embodiment of the present invention, sensor 14 is a flow sensor that detects the flow of fluid in patient circuit 8. This flow can be used to determine the volume of fluid provided to the patient It is to be understood, however, that the present invention contemplates using other parameters, such as the power or current provided to a blower, to determine the flow and, hence, the volume of fluid provided to a patient. A pressure sensor 18 detects the pressure of the pressurized fluid in patient circuit 8 and, more particularly, at patient interface 12 and supplies to controller 16 a signal indicative of the detected pressure. While the point at which the flow is measured by flow sensor 14 and the pressure is measured by pressure sensor 18 are illustrated as being within ventilator 2, it is to be understood that the location at which the actual flow and pressure measurements are taken be anywhere along patient circuit 8 or patient interface 12 so long as the purpose of measuring the pressure at the patient and the volume of fluid delivered to the patient can be determined.

The present invention also contemplates providing one or more patient monitors 19 to detect other physiological conditions of the patient. Such physiological conditions can be used to monitor the patient and/or control the operation of ventilator 2. For example, one embodiment of the present invention contemplates that patient monitor 19 is a diaphragm electromyographic ("EMG") detection system that detects the EMG signals produced by the diaphragm during breathing. Another example of a suitable patient monitor is an effort detector, which detects the movement of the patient's chest during respiration. Patient monitor 19 is connected to controller 16, which monitors the diaphragm EMG or effort signal supplied thereto from patient monitor 19, for example, and, in one embodiment, causes ventilator 2 to supply fluid to patient 10 during an inspiratory phase of a respiratory cycle and to terminate or reduce the supply of fluid to patient 10 during an expiratory phase. More specifically, in this embodiment of the present invention, controller 16 signals pressure regulator 6 to supply pressurized fluid to patient 10 during an inspiratory phase and to withhold or reduce the supply of pressurized fluid to patient 10 during an expiratory. Alternatively, as shown by dashed line 25 between controller 16 and pressurized fluid source 4, controller 16 can control pressurized fluid source 4 directly to supply pressurized fluid to patient 10 during inhalation and to withhold or reduce the supply of pressurized fluid from patient 10 during exhalation, thereby effectively incorporating the function of pressure regulator 6 into pressurized fluid source 4.

While the use of the diaphragm EMG or effort signal has been described above as the mechanism for triggering the ventilator, it is to be understood that the present invention contemplates using any conventional ventilator triggering technique suitable for use with a spontaneously breathing patient. For example, the pressure and/or flow generated by the patient in patient interface 12 and/or patient circuit 8 can be used to trigger the ventilator. In addition, ventilator 2, and, more specifically, controller 16, can include a timed backup so that if the patient stops breathing for a period of time exceeding a predetermined threshold, the ventilator automatically initiates a breathing cycle.

Pressurized fluid source 4 is, for example, a source of compressed gas, e.g., air, oxygen, helium-oxygen, or other oxygen mixture. The present invention also contemplates that pressurized fluid source is a piston, a bellows or a blower that receives a supply of gas, either from ambient atmosphere or a source of compressed gas, and generates a flow of such gas. Pressure regulator 6 is, for example, a poppet, solenoid, butterfly, rotary, sleeve, or any other valve or valve assembly suitable for use in controlling a flow and/or pressure of fluid delivered to a patient. As noted above controller 16 can control the pressure and/or flow of fluid from pressurized fluid source 4 directly, i.e., without the need for a dedicated pressure control valve, by controlling the speed of the piston, bellows, or blower, thereby effectively combining the functions of pressurized fluid source 4 and pressure regulator 6 as a single unit, as generally indicated by dashed line 27. For present purposes, the combined function of the source of pressurized fluid 4 and a pressure regulator 6 is referred to as a "pressure generating system." Thus, the pressure generating system includes pressurized fluid source 4 alone, if the flow/pressure of fluid output by the pressurized fluid source can be controlled directly, for example by regulating blower speed, otherwise the pressure generating system includes the combination of source of pressurized fluid 4 and pressure regulator 6.

In one embodiment of the present invention, patient circuit 8 is a single tube or conduit 20 connected between pressure regulator 6 and interface 12, typically referred to as a single-limb circuit. In this embodiment, conduit 20 and/or patient interface 12 includes an exhaust assembly 22 that vents exhaled gases to atmosphere and, thus, represents a known leak in the breathing gas delivery system. An example of a passive exhaust assembly is a hole or slot formed in conduit 20 and/or interface 12 that communicates the interior of the conduit or interface with atmosphere, with no active control over the flow of gas from the system, thereby providing a flow of exhaust gas from the patient circuit and/or interface. The size of the hole is typically selected to be sufficient to purge exhaled gas from the patient circuit. It is to be understood, however, that a wide variety of exhaust devices and configurations are contemplated for use with the ventilator/pressure generating system of the present invention. For example, U.S. Pat. No. 5,685,296 to Zdrojkowski et al. discloses an exhalation device and method where the exhalation flow rate through the device remains substantially constant over a range of pressures in the patient circuit. This exhalation device, which is commonly referred to as a plateau exhalation valve or PEV, is suitable for use with the pressure support system of the present invention.

In another embodiment of the present invention, patient circuit 8 includes a second tube or conduit illustrated by dashed line 24 in FIG. 1, which is typically referred to as a two-limb circuit. Second tube or conduit 24 communicates fluid exhaled by patient 10 to ventilator 2, which includes an active exhaust assembly that monitors and/or controls the venting of exhaust fluids to atmosphere. An example of an active exhaust assembly is a valve that prevents fluid from exhausting to atmosphere when pressurized fluid is supplied to patient 10, i.e., during the inspiratory phase, and that allows gas to escape to atmosphere when the supply of pressurized fluid to patient 10 is terminated or reduced, i.e., during the expiratory phase. Typically, the active exhaust assembly controls the flow of exhaust gas to atmosphere to control the positive end exhalation pressure ("PEEP") in the patient. Of course, the active exhaust need not be provided in the actuation housing of the ventilator, as generally shown in FIG. 1, but, regardless of its actual location, is typically controlled by or based on signals provided by the ventilator.

The present invention contemplates that patient interface device 12 is any device, either invasive or non-invasive, suitable for communicating a flow of breathing gas from the patient circuit to an airway of the patient. Examples of suitable patient interface devices include a nasal mask, nasal/oral mask, full-face mask, tracheal tube, endotracheal tube, and nasal pillow.

As described in detail below, the present invention contemplates adjusting the IPAP level, which is referred to as $IPAP_{set}$, from one inspiratory phase to the next so that the average volume over multiple breaths corresponds to a target average volume. It is believed that by varying the IPAP level for the delivery of breathing gas to the patient so as to achieve an average volume over multiple breaths, rather than a target volume for each breath as done in the VTV or VAPS mode, for example, the ventilation mode of the present invention is more comfortable for the spontaneously breathing patient while still being responsive to the patient's changing respiratory demands.

Determining the average volume over multiple breath cycles requires determining the volume of breathing gas $V_T$ delivered during each breath. This is accomplished relatively easily in a two-limb patient circuit because the ventilator controls the amount of fluid exhausted to atmosphere. In addition, there is considered to be substantially no leak from the patient circuit in a two-limb configuration. Therefore, the total volume of breathing gas delivered to the patient during each breath $V_T$ is determined using any conventional technique, such by providing a flow meter in the exhaust limb to measure the flow rate of exhaust gas and, from this, determine the volume of gas exhausted during each breath cycle, which corresponds to $V_T$.

In a single limb circuit, however, determining the volume of breathing gas actually delivered to or received by the patient during each breath $V_T$ is more difficult due to the fact that there is a relatively large intentional leak in the patient circuit and potential unintentional leaks at the interface between the patient and the interface device. U.S. Pat. No. 5,148,802 to Sanders et al., U.S. Pat. No. 5,313,937 to Zdrojkowski et al., U.S. Pat. No. 5,433,193 to Sanders et al., U.S. Pat. No. 5,632,269 to Zdrojkowski et al., and U.S. Pat. No. 5,803,065 to Zdrojkowski et al., the contents of each of which are incorporated by reference into the present invention, describe techniques for detecting and estimating leak and managing the delivery of breathing gas to the patient in the presence of leaks. Although one can refer to one or more of these patents to determine how to estimate leak rate in a single-limb circuit for the purpose of determining the total flow to the patient during a breathing cycle, a brief description of this process is provided below for the sake of completeness.

In a single limb circuit, the volume of fluid $V_T$ received by patient 10 over a breath cycle is determined from a difference between the volume of fluid supplied to the patient by the ventilator, i.e., the volume of fluid output by the ventilator, and the volume of fluid leaking from the ventilator system, which includes leak from the patient circuit and leak from the patient interface device, during that breath cycle. Typically, most of the leak is from the exhaust vent in the patient circuit. More specifically, fluid leaking to atmosphere is generally the result of a known leak, such as the exhaust flow provided by exhaust assembly 22 in the single-limb circuit, and unknown leaks, such as a leak at the interface between the patient and patient interface device 12. The flow of fluid received by patient 10 at any given time is estimated using Equation 1:

$$\dot{V}_{est} = \dot{V}_{tot} - \dot{V}_{leak}, \quad (1)$$

where:

$\dot{V}_{est}$=estimated flow of fluid received by patient 10;
$\dot{V}_{tot}$=flow of fluid supplied to patient 10 by the pressure support device at that time; and
$\dot{V}_{leak}$=estimated flow of fluid leaking into the atmosphere at that time.

As used herein, the "$\dot{V}$" notation refers the derivative of volume with respect to time, which is commonly referred to as "flow".

While Equation 1 defines the estimated flow to the patient at any instant during a breath cycle, a similar relationship exists for estimating the total volume of fluid $V_{est}$ delivered to the patient during a breath cycle and is defined as follows:

$$V_{est} = V_{tot} - V_{leak}, \quad (2)$$

where:

$V_{est}$=estimated volume of fluid received by patient 10 during the breathing cycle and corresponds to $V_T$;
$V_{tot}$=volume of fluid supplied to patient 10 by the pressure support device during the breathing cycle; and
$V_{leak}$=estimated volume of fluid leaking into the atmosphere over the breathing cycle.

According to one leak estimation technique, $\dot{V}_{leak}$ in Equation 1 is determined as a function of the conductance between interface 12 and patient 10. For simplicity of determining $\dot{V}_{leak}$ in Equation 1, conductance $G_{leak}$ between interface 12 and patient 10 is assumed to be a constant for each breath cycle and is determined using the following Equation 3:

$$G_{leak} = \frac{\int_0^{T_{breath}} \dot{V}_{tot}(t) dt}{\int_0^{T_{breath}} \sqrt{P_{interface}(t)}\, dt}, \quad (3)$$

where:

$G_{leak}$=conductance between interface 12 and patient 10 during the inspiratory phase;
$P_{interface}$=fluid pressure determined at or near interface 12, which is a value measured using pressure sensor 18, for example; and
$\dot{V}_{tot}$=flow of fluid supplied to patient 10, which is also a value measured using flow sensor 14, for example.

Conductance $G_{leak}$ determined using Equation 2 is utilized in the following Equation 4 to estimate the flow of fluid leaking into the atmosphere, i.e., $\dot{V}_{leak}$, at any given time:

$$\dot{V}_{leak} = G_{leak} \sqrt{P_{interface}}. \quad (4)$$

During a breathing cycle, controller 2 monitors the flow of fluid supplied to patient 10 ($V_{tot}$) via flow sensor 14 and the fluid pressure determined at or near interface 12 ($P_{interface}$) via pressure sensor 18. Using this information gathered over a complete breathing cycle, controller determines the value for $$\int_0^{T_{breath}} \dot{V}_{tot}(t) dt \text{ and } \int_0^{T_{breath}} \sqrt{P_{interface}(t)}\, dt,$$

which are the terms in the numerator and denominator, respectively, for Equation 3. In an exemplary embodiment of the present invention, controller 16 samples the signals generated by flow sensor 14 and pressure sensor 18 a plurality of times, for example, 100 samples per breath cycle, to obtain $\dot{V}_{tot}$ and $P_{interface}$ during that breath cycle. Once the values for $$\int_0^{T_{breath}} \dot{V}_{tot}(t) dt \text{ and } \int_0^{T_{breath}} \sqrt{P_{interface}(t)}\, dt$$

are obtained, Equation 3 can be solved so that the conductance ($G_{leak}$) associated with a particular breathing cycle is known.

To determine a value for $\dot{V}_{leak}$ at any given instant in a breath cycle, controller 16 solves Equation 4 utilizing the known value of conductance $G_{leak}$, and the fluid pressure in interface 12 at that instant, which is preferably measured using pressure sensor 18. It is to be understood that the present invention contemplate using an average value of conductance $G_{leak}$, rather than the conductance determined in the immediately preceding breath cycle. For example, the conductance for each of the last n breath(s) can be calculated and the average conductance over the n breath(s) can be used in Equation 4 to determine leak, where n is an integer. The present invention also contemplates that numerator, the denominator, or both in Equation 3 can be determined from an average of these values determined during the last n breaths.

Another technique for determine conductance $G_{leak}$ at breath cycle n+1 involves solving the following equations 5–7:

$$N_{n+1} = \frac{N_n}{2} + \int_0^{T_{breath}} (\dot{V}_{tot} - \dot{V}_{known\ leak}), \quad (5)$$

$$D_{n+1} = \frac{D_n}{2} + \int_0^{T_{breath}} \sqrt{P_{interface}}, \quad (6)$$

$$G_{leak\ n+1} = \frac{N_{n+1}}{D_{n+1}}, \quad (7)$$

where $\dot{V}_{known\ leak}$ is a predetermined known leak from the patient circuit, typically through the exhaust, port for a given pressure in the patient circuit, which is measured by pressure sensor 18, for example.

In an exemplary embodiment of the present invention, controller 16 determines $\dot{V}_{leak}$ by sampling the fluid pressure $P_{interface}$ multiple times, such as 100 times, during the breathing cycle. For each sampled pressure, controller 16 calculates $\dot{V}_{leak}$ using Equation 4, with the known value of conductance $G_{leak}$ used in Equation 4 being obtained using any of the above-described techniques. By sampling the pressure multiple time during the breath cycle and determining $\dot{V}_{leak}$ at each sample, controller 16 closely approximates the total leak volume $V_{leak}$ during the entire breath cycle. Knowing the total leak volume $V_{leak}$ for the current breath cycle and the total volume $V_{tot}$ of fluid supplied to patient 10 by the pressure support device during the current breathing cycle, which is readily determined from the measured flow, controller 16 solves Equation 2 to determine a value for the total volume $V_{est}$ of fluid delivered to the patient during the current breath cycle.

Figure 2A:
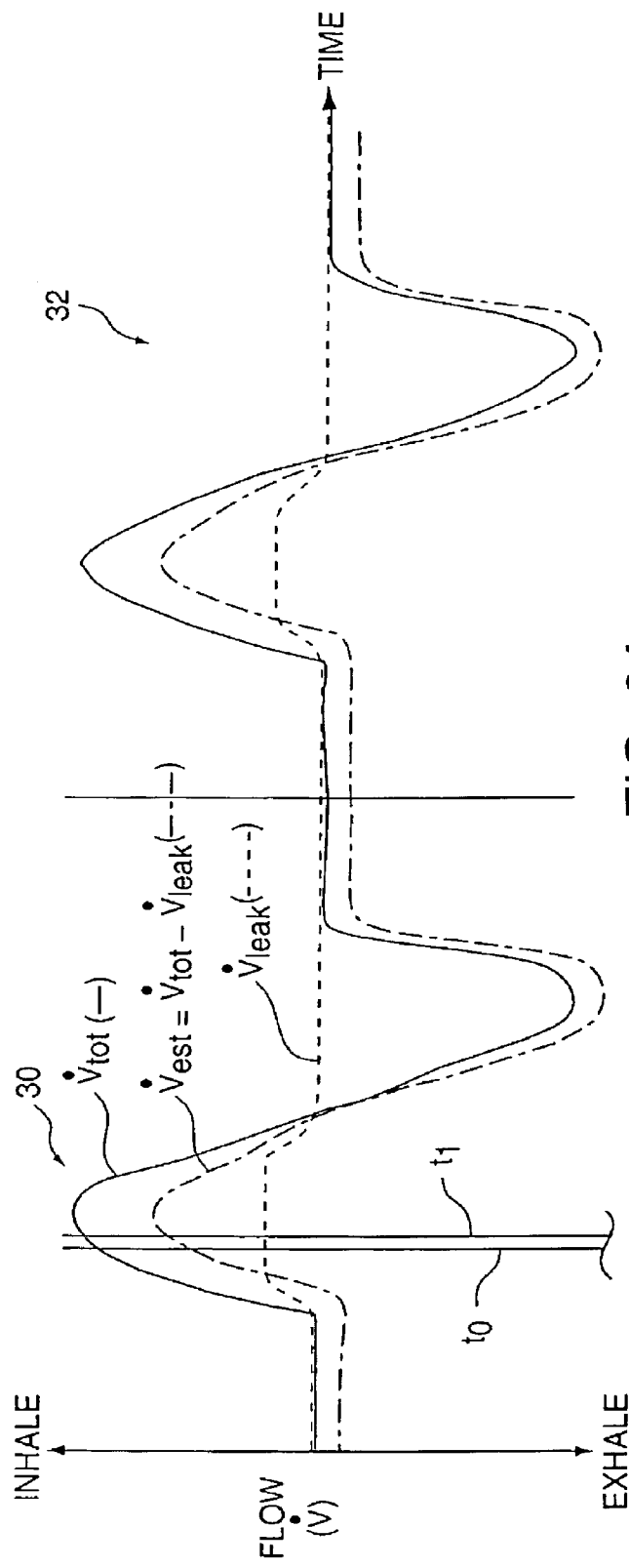
FIG. 2A is a time-based graph of fluid flow supplied to the patient $\dot{V}_{est}$, fluid flow leaked from the system, typically into the atmosphere $\dot{V}_{leak}$, and fluid flow received by the patient $\dot{V}_{tot}$ in response to operation of the ventilator shown in FIG. 1 during a single breath cycle.
Figure 2B:
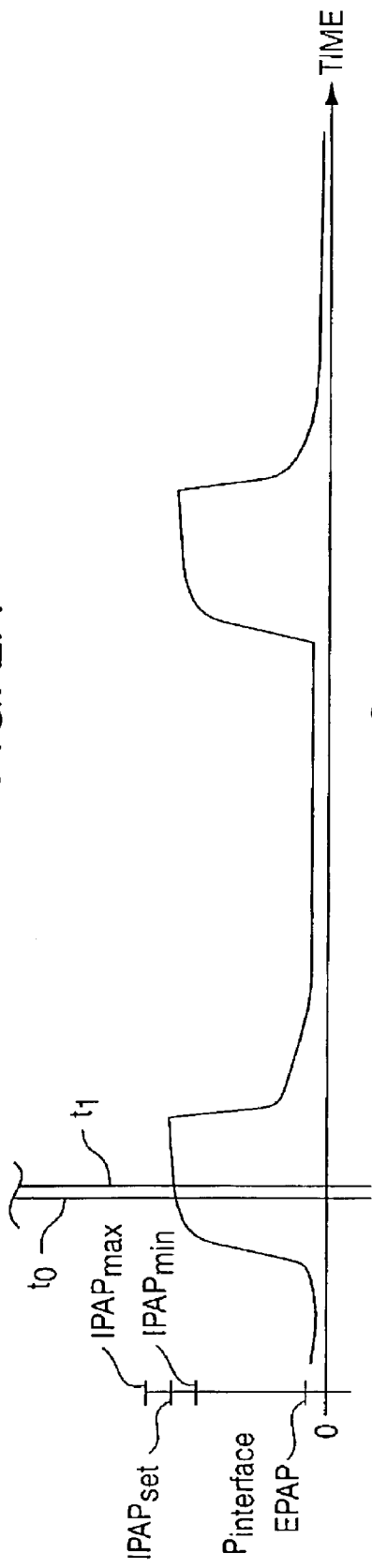
FIG. 2B is a time-based graph of fluid pressure at the interface shown in FIG. 1 in response to operation of the ventilator.

For example, as shown in FIGS. 2A–2B, at time $t_0$, during a first breath cycle 30, controller 16 samples the signal from flow sensor 14 and samples the signal from pressure sensor 18 to obtain instantaneous values of fluid flow $\dot{V}_{tot}$ (FIG. 2A) and fluid pressure $P_{interface}$ (FIG. 2B). At time $t_1$ during first breath cycle 30, controller 16 again samples the signals from flow sensor 14 and pressure sensor 18 to obtain instantaneous values of fluid flow $\dot{V}_{tot}$ and fluid pressure $P_{interface}$. Sampling the signals generated by flow sensor 14 and pressure sensor 18 a plurality of times during first breath cycle 30 enables controller 16 to determine a value for $$\int_0^{T_{breath}} \dot{V}_{tot}(t)dt \text{ and a value for } \int_0^{T_{breath}} \sqrt{P_{interface}(t)}\ dt$$

for first breath cycle 30. Utilizing the thus obtained values for first breath cycle 30, controller 16 solves Equation 3 to obtain a value for conductance $G_{leak}$ for first breath cycle 30.

During a second breath cycle 32, controller 16 obtains a plurality of samples of the signals from flow sensor 14 and pressure sensor 18. Controller 16 stores this information for second breath cycle 32 and utilizes the plural samples of the signals from flow sensor 14 and pressure sensor 18 to determine values for $\dot{V}_{tot}$ and $$\int_0^{T_{breath}} \sqrt{P_{interface}(t)}\ dt$$

for second breath cycle 32. Controller 16 uses the thus determined values to solve Equation 3 to obtain a value for conductance $G_{leak}$ for second breath cycle 32.

Next, controller 16 utilizes conductance $G_{leak}$ determined for first breath cycle 30 and the samples pressures $P_{interface}$ determined for second breath cycle 32 to solve Equation 4 for each sampled pressure to obtain a value for $\dot{V}_{leak}$ for second breath cycle 32. Using the values for $\dot{V}_{tot}$ and $\dot{V}_{leak}$ determined at multiple samples through the second breath cycle 32, controller 16 determines the total volume of fluid delivered by the pressure support device $V_{tot}$ and and total volume $V_{leak}$ or fluid that leaked from the patient circuit during the second breath cycle. Controller 16 then solves Equation 2 to determine the estimated volume of fluid $V_{est}$ received by the patient during second breath cycle 32. In a similar manner, controller 16 determines for a third breath cycle (not shown) values for $$\dot{V}_{tot}, \int_0^{T_{breath}} \dot{V}_{tot}(t)dt, \int_0^{T_{breath}} \sqrt{P_{interface}(t)}\ dt,$$

$G_{leak}$, and $\dot{V}_{leak}$. Using the value of conductance $G_{leak}$ determined for second breath cycle 32 and the pressure samples taken during the third breath cycle, controller 16 solves Equation 4 to obtain values for $\dot{V}_{leak}$ during each sample taken during the third breath cycle. Using the values of $\dot{V}_{tot}$ and $\dot{V}_{leak}$ determined for the multiple samples in the third breath cycle, controller 16 determines the total volume of fluid delivered by the pressure support device $V_{tot}$ and and total volume $V_{leak}$ or fluid that leaked from the patient circuit during the third breath cycle. Controller 16 then solves Equation 2 to determine the estimated volume of fluid $V_{est}$ for the third breath cycle. In a similar manner, controller 16 determines values for $V_{est}$ for subsequent breath cycles.

As noted above, preferably controller 16 solves Equation 4 to obtain a value for $\dot{V}_{leak}$ for each sample in a breath cycle as a function of conductance $G_{leak}$ determined from the immediately preceding breath cycle and $P_{interface}$ determined at each sample. Conductance $G_{leak}$ used in Equation 4, however, as noted above, can be an average conductance ("AVG $G_{leak}$") determined from a plurality of preceding breath cycles. Moreover, controller 16 can determine a value for the total leak during a breath cycle $\dot{V}_{leak}$ from conductance $G_{leak}$ and the values of $P_{interface}$ taken during that same breath cycle.

For a detailed description of leak detection and management of patient flow in the presence of leaks, see the above identified patents of Sanders et al. and Zdrojkowski et al., and, in particular, U.S. Pat. No. 5,803,065 to Zdrojkowski et al., the contents of which were incorporated herein by reference above.

Controller 16 can also determine for each breath cycle a value for $\dot{V}_{est}$ in Equation 1 using regression analysis.

As shown in FIG. 2B, when pressurized fluid is supplied to patient 10 during first breath cycle 30, pressure regulator 6 sets the inspiratory positive airway pressure ("IPAP") level for the fluid delivered to patient 10, which is identified as IPAP$_{set}$ in FIG. 2B and is preferably between a maximum IPAP, IPAP$_{max}$, and a minimum IPAP, IPAP$_{min}$. IPAP$_{max}$ and IPAP$_{min}$ are typically set by the clinician. However, the present invention also contemplates that IPAP$_{max}$, IPAP$_{min}$ or both can be automatically set by the ventilator. For example, once the user sets IPAP$_{min}$, the ventilator can set IPAP$_{max}$ automatically as a fixed percentage of fixed pressure above IPAP$_{min}$. IPAP$_{min}$ can be set in a similar fashion after the clinician set IPAP$_{max}$.

Using the above techniques, the system of the present invention determines the volume of fluid $V_T$ delivered to a patient during a breath cycle. As noted above, if the system is a single-limb circuit, i.e., a circuit with a leak, the volume of fluid $V_T$ delivered to a patient during a breath cycle is estimated as $V_{est}$.

Figure 3:
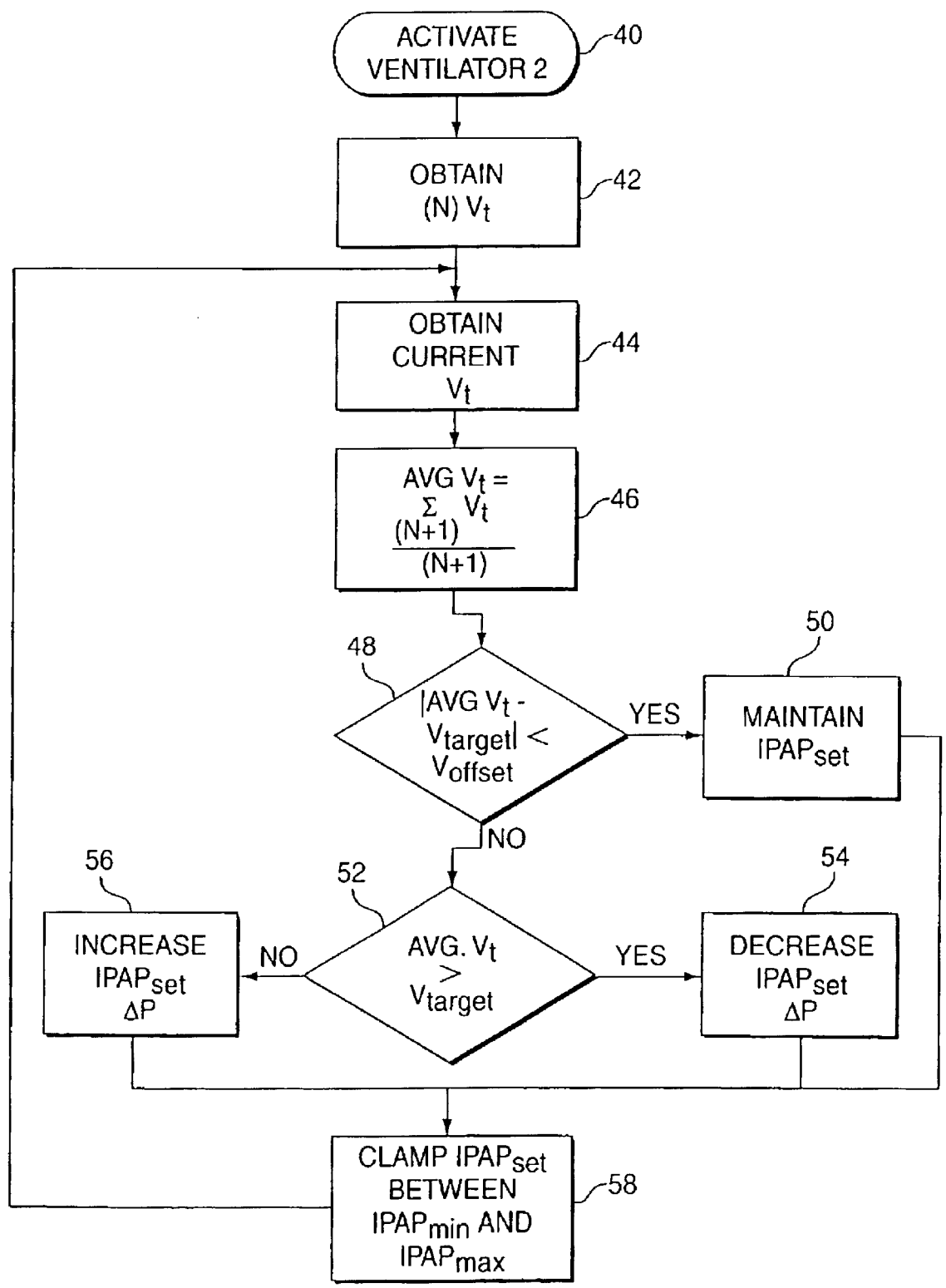
FIG. 3 is a flow chart of the operation of the ventilator in accordance with the present invention.

With reference to FIG. 3, and referring back to FIG. 1, the method for adjusting a volume of fluid supplied to a patient $V_T$ from one inspiratory phase to the next in a manner that is comfortable for the patient and responsive to the patient's changing respiratory demands will now be described. According to the principles of the present invention, adjusting a volume of fluid supplied to a patient $V_T$ is accomplished by controller 16 causing pressure regulator 6 to adjust IPAP$_{set}$ in accordance with the steps set forth in the flow chart shown in FIG. 3.

In response to activating ventilator 2 in step 40, controller 16 causes pressurized fluid to be supplied to patient 10 during the inspiratory phase and causes the flow of pressurized fluid to be reduced or withheld from patient 10 during exhalation. In step 42, controller 16 determines N values of $V_T$, where N is at least one (1) or more and preferably five (5). Each value of $V_T$ is determined in the above-described manner and corresponds to the estimated volume $V_{est}$ of fluid received by patient 10 during a corresponding breath cycle if the patient circuit is a single limb circuit. In step 44, controller 16 determines a current value of $V_T$ and in step 46, controller 16 determines an average value of $V_T$ ("AVG $V_T$") for N+1 breath cycles. In step 48, controller 16 compares an absolute value of the difference between AVG $V_T$ and a predetermined target volume of fluid $V_{target}$ to be received by patient 10 to a predetermined offset value $V_{offset}$. If this absolute value is less than the predetermined offset value $V_{offset}$, controller 16 branches to step 50 where the current value of IPAP$_{set}$ is maintained. The predetermined target value of fluid $V_{target}$ is determined clinically for each patient 10 and the predetermined offset value $V_{offset}$ can be a set value or a programmable value established by ventilator 2.

If the absolute value of the difference between AVG $V_T$ and $V_{target}$ is greater than or equal to $V_{offset}$, controller 16 branches to step 52. In step 52, controller 16 determines if AVG $V_T$ is greater than $V_{target}$. If so, controller 16 branches to step 54. In step 54, controller 16 causes pressure regulator 6 to decrease IPAP$_{set}$ by a predetermined pressure ΔP, e.g., 0.1 cm H$_2$O. If, however, in step 52 controller 16 determines that AVG $V_T$ is less than $V_{target}$, controller 16 branches to step 56. In step 56, controller 16 causes pressure regulator 6 to increase IPAP$_{set}$ by the predetermined pressure ΔP. Increasing or decreasing IPAP$_{set}$ increases or decreases, respectively, the volume of fluid $V_T$ delivered to patient 10 during the inspiratory phase.

To avoid undesirably high or low values of IPAP$_{set}$, in step 58, controller 16 compares the current IPAP$_{set}$ to IPAP$_{max}$ and IPAP$_{min}$. If the current IPAP$_{set}$ is greater than IPAP$_{max}$, in step 58, controller 16 causes pressure regulator 6 to clamp the current value of IPAP$_{set}$ to IPAP$_{max}$. Similarly, if the current value of IPAP$_{set}$ is less than IPAP$_{min}$, in step 58, controller 16 causes pressure regulator 6 to clamp the current value of IPAP$_{set}$ to IPAP$_{min}$. After completing step 58, controller 16 repeats steps 44–58 for each subsequent breath cycle.

It can thus be appreciated that step 46 determines AVG $V_T$ for the current breath cycle and N prior breath cycles. Hence, step 46 determines a moving average of AVG $V_T$, which is utilized in steps 48 and 52. Alternatively, steps 42 and 46 can be eliminated and the current value of $V_T$ can be utilized in place of AVG $V_T$ in steps 48 and 50.

In a two-limb circuit, with the patient coupled to an invasive patient interface device, such as a trachea tube or an endotracheal tube, there is considered to be substantially no leak. Thus, $V_T=V_{tot}$, which is measured directly by flow sensor 14 in FIG. 1, for use in the routine shown in FIG. 3. Therefore, in this embodiment, the determination of $V_T$ is simplified and need not be calculated using the analysis discussed above.

In the illustrated embodiment as noted above, the volume delivered to the patient is averaged over two or more, and preferably 6, breaths to determine (step 46 in FIG. 3) whether to maintain (steps 48 and 50), decrease (step 52 and 54), or increase (steps 52 and 56) IPAP by an incremental amount. However, the present invention also contemplates using the patient's minute ventilation, which is a parameter that is widely understood and generally familiar to those in the health care industry, instead of the volume averaged over a number of breaths, AVG $V_T$, to determine whether to modify IPAP. Thus, the present invention contemplates altering steps 46–52 in FIG. 3 so that the minute ventilation ("MV") replaces AVG $V_T$.

Based on the foregoing, it can be appreciated that the present invention provides an apparatus and method for adjusting the volume of fluid supplied to a patient during a breathing cycle as a function of the volume of fluid received by the patient during a previous breathing cycle, thereby avoiding patient discomfort. This allows the patient to alter his or her breathing pattern temporality, such as by taking a very shallow or a very deep breath, during one breathing cycle without the ventilator overreacting to these minor variation.

The invention has been described with reference to the preferred embodiments. Obvious modifications and alterations will occur to others upon reading and understanding the preceding detailed description. It is intended that the invention be construed as including all such modifications and alterations insofar as they come within the scope of the appended claims or the equivalents thereof.

What is claimed is:

1. A method of adjusting a volume of a fluid supplied to a patient, the method comprising the steps of:

(a) supplying a plurality of volumes of fluid to a patient during a like plurality of inspiratory phases of a respiratory cycle of such a patient, each volume of fluid being supplied at an inspiratory positive airway pressure during a corresponding inspiratory phase;

(b) determining, for each inspiratory phase, a tidal volume of fluid received by such a patient;

(c) determining an average tidal volume of fluid received by such a patient from the volumes of fluid received by such a patient during the plurality of inspiratory phases, wherein the average tidal volume is determined irrespective of a period of time during which the plurality of inspiratory phases occur;

(d) comparing the average tidal volume to a predetermined target tidal volume;

(e) adjusting the inspiratory positive airway pressure based on the comparison;

(f) comparing a current inspiratory positive airway pressure to a maximum inspiratory positive airway pressure and a minimum inspiratory positive airway pressure; and (g) preventing adjusting of the inspiratory positive airway pressure in step (e) if one of (1) the current inspiratory positive airway pressure is greater than the maximum inspiratory positive airway pressure and (2) the current inspiratory positive airway pressure is less than the minimum inspiratory positive airway pressure.

2. An apparatus for supplying fluid to a patient, the apparatus comprising:

a pressure generating system adapted to provide a flow of fluid at one of a variable pressure and a variable flow;

a patient circuit operatively coupled to the pressure generating system to deliver the flow of fluid to a patient;

an interface device operatively coupled to the patient circuit to communicate the flow of fluid to an airway of a patient;

at least one sensor operatively coupled to one of the pressure generating system, the patient circuit, and the interface device to detect a parameter indicative of a volume of fluid delivered to such a patient; and a controller operatively coupled to the sensor and the pressure generating system, wherein the controller:
  (a) determines, for each inspiratory phase of a respiratory cycle of such a patient, a tidal volume of fluid received by such a patient based on the parameter indicative of a volume of fluid delivered to such a patient provided by the sensor;
  (b) determines an average tidal volume of fluid received by such a patient over a plurality of inspiratory phases, wherein the average tidal volume is determined irrespective of a period of time during which the plurality of inspiratory phases occur;
  (c) compares the average tidal volume of fluid received by such a patient to a predetermined target tidal volume;
  (d) causes the pressure generating system to adjust pressure, a rate of flow of fluid output thereby, or both based on the comparison; and
  (e) prevents adjusting of the pressure or the rate of flow of fluid output by the pressure generating system if (1) the current pressure is greater than a predetermined maximum pressure or (2) the current pressure is less than a predetermined minimum pressure.

3. An apparatus for supplying fluid to a patient, the apparatus comprising:

pressure generating means for providing a flow of fluid at one of a variable pressure and a variable flow rate;

delivering means for delivering the flow of fluid to a patient;

interfacing means for communicating the flow of fluid to an airway of a patient;

sensing means for sensing a parameter indicative of a volume of fluid delivered to such a patient; and processing means for:
  (a) determining, for each inspiratory phase of a respiratory cycle of such a patient, a tidal volume of fluid received by such a patient based on the parameter indicative of a volume of fluid delivered to such a patient provided by the sensing means;
  (b) determining an average tidal volume of fluid received by such a patient over a plurality of inspiratory phases, wherein the average tidal volume is determined irrespective of a period of time during which the plurality of inspiratory phases occur;
  (c) comparing the average tidal volume of fluid received by such a patient to a predetermined target tidal volume;
  (d) causing the pressure generating means to adjust a pressure, a rate of flow of fluid output thereby, or both based on the comparison; and
  (e) preventing adjusting of the pressure or the rate of flow of fluid output by the pressure generating system if (1) the current pressure is greater than a predetermined maximum pressure or (2) the current pressure is less than a predetermined minimum pressure.

4. An apparatus for adjusting a volume of a fluid supplied to a patient, the apparatus comprising:

supplying means for supplying a plurality of volumes of fluid to a patient during a like plurality of inhalations by such a patient, with each volume of fluid supplied at an inspiratory positive airway pressure during a corresponding inspiratory phase;

tidal volume determining means for determining, for each inspiratory phase, a tidal volume of fluid received by such a patient;

average tidal volume determining means for determining an average tidal volume of fluid received by such a patient from the tidal volumes of fluid received by such a patient during the plurality of inspiratory phases, wherein the average tidal volume is determined irrespective of a period of time during which the plurality of inspiratory phases occur;

comparing means for comparing the average tidal volume to a predetermined target tidal volume;

adjusting means for adjusting the inspiratory positive airway pressure based on the comparison;

comparing means for comparing a current inspiratory positive airway pressure to a maximum inspiratory positive airway pressure and a minimum inspiratory positive airway pressure; and preventing means for preventing adjusting of the inspiratory positive airway pressure if (1) the current inspiratory positive airway pressure is greater than the maximum inspiratory positive airway pressure or (2) the current inspiratory positive airway pressure is less than the minimum inspiratory positive airway pressure.

5. An apparatus for supplying a desired volume of a fluid to a patient, the apparatus comprising:

supplying means for supplying a first volume of fluid to a patient at a first inspiratory positive airway pressure;

determining means for determining, for the first volume of fluid supplied to such a patient, a first tidal volume of fluid received by such a patient, wherein the supplying means supplies a second volume of fluid to such a patient at the first inspiratory positive airway pressure, and wherein the determining means determines, for the second volume of fluid supplied to such a patient, a second tidal volume of fluid received by such a patient;

averaging means for determining, based on the first and the second tidal volumes of fluid received by such a patient, a first average tidal volume of fluid received by such a patient, wherein the first average tidal volume is determined irrespective of a period of time during which the plurality of inspiratory phases occur;

comparing means for comparing the first average tidal volume to a predetermined target tidal volume;

adjusting means for adjusting the first inspiratory positive airway pressure to a second inspiratory positive airway pressure based on the comparison of the first average volume to the predetermined target volume;

comparing means for comparing a current inspiratory positive airway pressure to a maximum inspiratory positive airway pressure and a minimum inspiratory positive airway pressure; and preventing means for preventing adjusting of the inspiratory positive airway pressure if (1) the current inspiratory positive airway pressure is greater than the maximum inspiratory positive airway pressure or (2) the current inspiratory positive airway pressure is less than the minimum inspiratory positive airway pressure.

* * * * *